US012723037B2

(12) United States Patent
Zhu et al.

(10) Patent No.: US 12,723,037 B2
(45) Date of Patent: Sep. 1, 2026

(54) TRIAZOLE DERIVATIVE, METHOD FOR PREPARING SAME, AND USE THEREOF

(71) Applicant: SHENZHEN JIKANG PHARMACEUTICAL TECHNOLOGY CO., LTD., Shenzhen (CN)

(72) Inventors: Yongqiang Zhu, Shenzhen (CN); Meng Lei, Shenzhen (CN); Hang Miao, Shenzhen (CN); Xueyuan Wang, Shenzhen (CN)

(73) Assignee: SHENZHEN JIKANG PHARMACEUTICAL TECHNOLOGY CO., LTD., Shenzhen (CN)

( * ) Notice: Subject to any disclaimer, the term of this patent is extended or adjusted under 35 U.S.C. 154(b) by 426 days.

(21) Appl. No.: 18/277,099

(22) PCT Filed: Mar. 11, 2022

(86) PCT No.: PCT/CN2022/080255
§ 371 (c)(1),
(2) Date: Aug. 14, 2023

(87) PCT Pub. No.: WO2022/188846
PCT Pub. Date: Sep. 15, 2022

(65) Prior Publication Data

US 2024/0140934 A1 May 2, 2024

(30) Foreign Application Priority Data

Mar. 12, 2021 (CN) ......................... 202110267569.4

(51) Int. Cl.
*C07D 403/06* (2006.01)

(52) U.S. Cl.
CPC .................................. *C07D 403/06* (2013.01)

(58) Field of Classification Search
CPC ........ C07D 403/06; A61P 11/00; A61P 25/00; A61P 27/02; A61P 29/00; A61P 31/12; A61P 35/00; A61P 37/00; A61P 37/08; A61K 31/506
See application file for complete search history.

(56) References Cited

FOREIGN PATENT DOCUMENTS

CN 105339358 A 2/2016
WO WO-2014205389 A1 * 12/2014 .............. A61P 37/00

OTHER PUBLICATIONS

May 24, 2022 Search Report issued in International Patent Application No. PCT/CN2022/080255.

* cited by examiner

*Primary Examiner* — Umamaheswari Ramachandran
(74) *Attorney, Agent, or Firm* — Oliff PLC

(57) ABSTRACT

The technical field of pharmaceuticals. Disclosed are a triazole derivative, a method for preparing same, and use thereof. The triazole derivative has a structure as shown in formula I, and the triazole derivative of the present invention can be used as a CRM1 inhibitor for preparing a medicament for treating a disease related to CRM1 activity.

3 Claims, 1 Drawing Sheet

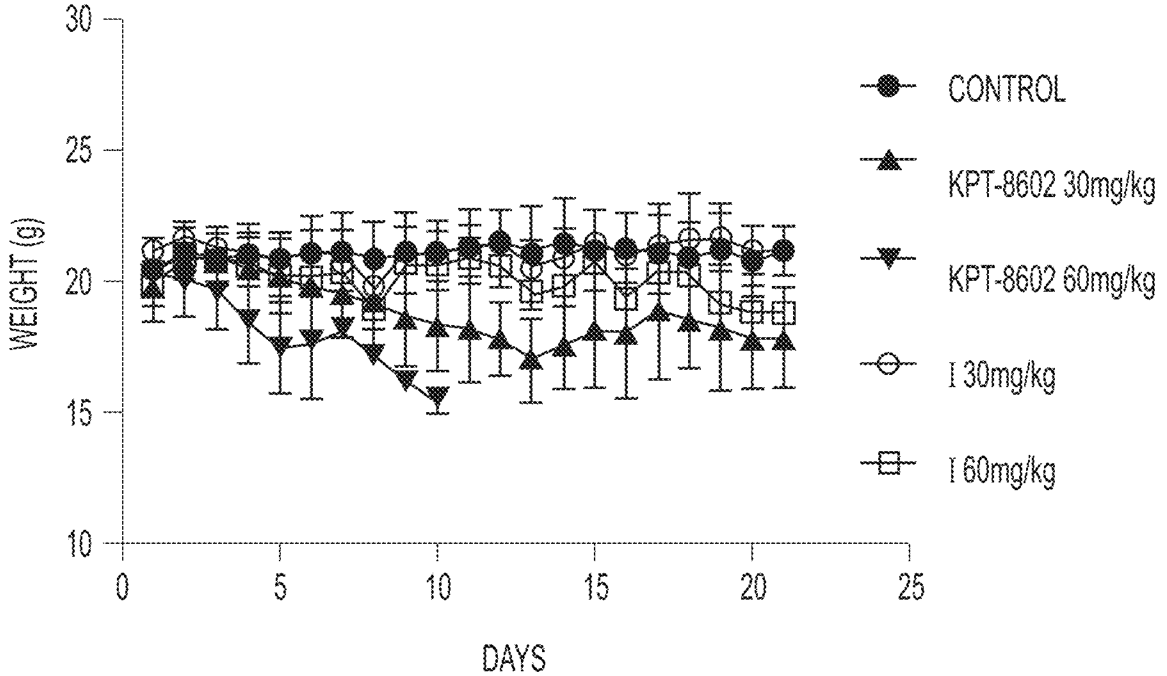
30
25
20
15
10
WEIGHT (g)
0
5
10
15
20
25
DAYS
CONTROL
KPT-8602 30mg/kg
KPT-8602 60mg/kg
I 30mg/kg
I 60mg/kg

TRIAZOLE DERIVATIVE, METHOD FOR PREPARING SAME, AND USE THEREOF

TECHNICAL FIELD

The present invention relates to the technical field of pharmaceuticals, and particularly to a triazole derivative, a method for preparing same, and use thereof.

BACKGROUND

At present, malignancies are still one of the major diseases threatening people's lives. Although the treatment of cancer has seen great progress, it has not yet been able to treat cancer fundamentally. Although the currently marketed anti-cancer drugs have certain curative efficacy, most of them are cytotoxic drugs with serious toxic and side effects. Therefore, how to study novel targeted anti-cancer drugs from effective tumor targets has become a task of top priority for pharmaceutical workers.

Cells from most major human solid and hematologic malignancies exhibit abnormal cellular localization of a variety of oncogenic proteins, tumor suppressor proteins, and cell cycle regulators. For example, certain p53 mutations may lead to localization in the cytoplasm rather than the nucleus. This results in the loss of normal growth regulation, despite intact tumor suppressor function. In other tumors, wild-type p53 is sequestered in the cytoplasm or is rapidly degraded, again resulting in the loss of its suppressor function. Restoration of appropriate nuclear localization of functional p53 protein can normalize some properties of neoplastic cells, restore sensitivity of cancer cells to DNA damaging agents, and lead to regression of established tumors. Similar data have been obtained from other tumor suppressor proteins such as forkhead (Sullivan) and c-Abl. In addition, abnormal localization of some tumor suppressors and growth regulatory proteins may be associated with the pathogenesis of autoimmune diseases. CRM1 inhibition may provide particularly meaningful utility in familial cancer syndromes (e.g., Li-Fraumeni syndrome caused by deletion of one p53 allele, and BRCA1 or BRCA2 cancer syndrome), wherein specific tumor suppressor proteins (TSPs) are deleted or dysfunctional, and an increase in TSP levels achieved by systemic (or local) administration of CRM1 inhibitors can help restore normal tumor suppressor function.

Specific proteins and RNAs are transported into and out of the nucleus by specific transport molecules, which are classified as importins if they transport molecules into the nucleus, and as exportins if they transport molecules out of the nucleus. Proteins that are transported into and out of the nucleus contain nuclear import/localization sequences (NLSs) or nuclear export sequences (NESs) that allow them to interact with the relevant transport factors. Chromosome region maintenance 1 (CRM1), also known as exportin-1 or XPO1, is the major exportin.

Inhibitors of CRM1 block the nuclear export of suppressor proteins and growth regulators such as p53, c-Ab1, p21, p27, pRB, BRCA1 IkB, ICp27, E2F4, KLF5, YAP1, ZAP, KIF5, HDAC4, HDAC5, or forkhead proteins (e.g., FOXO3a) that are associated with gene expression, cell proliferation, angiogenesis, and epigenetics. CRM1 inhibitors have been shown to induce apoptosis in cancer cells even in the presence of activating signals or growth-activating signals, without affecting normal (untransformed) cells. Most studies on the function of CRM1 have been performed using the natural product, leptomycin B (LMB). Leptomycin itself is highly toxic to tumor cells, but is difficult to use clinically due to its high gastrointestinal toxicity. Derivatization of LMB to improve drug-like properties may lead to compounds that retain anti-tumor activity and are better tolerated by animal tumor models. Thus, nuclear export inhibitors may have beneficial effects on neoplastic disorders and other proliferative disorders. To date, however, small-molecule, drug-like CRM1 inhibitors for use in vitro and in vivo still have certain drawbacks.

In addition to tumor suppressor proteins, CRM1 also exports several key proteins involved in many inflammatory processes, including IkB, NF-kB, Cox-2, RXRa, Commal, HIFI, HMGBI, FOXO, FOXP, and the like. Transcriptional activators of the nuclear factor xB (NF-kB/rel) family, named based on the discovery of the ability to trigger immunoglobulin x gene expression, can regulate the mRNA expression of various genes associated with inflammation, proliferation, immunity, and cell survival. Under basic conditions, an NF-kB protein inhibitor, called IkB, binds to NF-kB in the nucleus and the IKB-NF-kB complex inactivates the transcription function of NF-kB. In response to inflammatory stimuli, IkB dissociates from the IkBNF-kB complex, releasing NF-kB while restoring its potential transcriptional activity. Many signals that activate NF-kB do so by targeting IkB for proteolysis (phosphorylation of IkB renders it "marked" for ubiquitination and then proteolysis). The nuclear IkBa-MF-kB complex can be exported by CRM1 to the cytoplasm, where the complex dissociates, resulting in the reactivation of NF-kB. The ubiquitinated IkB can also dissociate from the NF-kB complex, restoring the transcriptional activity of NF-kB. Inhibition of CRM1-induced export in human neutrophils and macrophage-like cells (U937) by IMB not only results in accumulation of the transcriptionally inactive nuclear IkBa-NF-kB complex, but also prevents initial NF-kB activation, even upon cellular stimulation. In a different study, treatment with LMB inhibited IL-1β-induced NF-kB DNA binding (the first step in NF-kB transcriptional activation), 1L-8 expression, and intercellular adhesion molecule expression in pulmonary microvascular endothelial cells. COMMD1 is another nuclear inhibitor of the transcriptional activity of both NF-kB and hypoxia-inducible factor 1(HIF1). Blocking the nuclear export of COMMD1 by inhibiting CRM1 may result in increased inhibition of the transcriptional activity of NF-kB and HIF1.

CRM1 also mediates retinoid X receptor a (RXRa) transport. RXRa is highly expressed in the liver and plays a central role in regulating bile acid, cholesterol, fatty acid, steroid and xenobiotic metabolism, and homeostasis. During hepatitis, nuclear RXRa levels are significantly reduced, mainly due to inflammation-mediated nuclear export of RXRa by CRM1. In human liver-derived cells, LepB is able to prevent L-1B-induced increase in cytoplasmic RXRa levels.

The role of CRM1-mediated nuclear export in NF-kB, HIF-1, and RXRa signaling suggests that blocking nuclear export may be potentially beneficial to many inflammatory processes across multiple tissues and organs, including vasculature diseases (vasculitis, arteritis, polymyalgia rheumatica, and atherosclerosis), skin diseases, and rheumatic diseases (rheumatoid and related arthritis, psoriatic arthritis, spondyloarthropathy, crystal arthropathy, systemic lupus erythematosus, mixed connective tissue disease, myositis syndrome, dermatomyositis, inclusion body myositis, undifferentiated connective tissue disease, Sjogren's syndrome, scleroderma, and overlap syndrome, and the like).

Inhibition of CRM1 can affect gene expression by inhibiting/activating a series of transcription factors like ICp27, E2F4, KL5, YAP1, and ZAP.

Inhibition of CRM1 has potential therapeutic effects on many dermatologic syndromes, including inflammatory dermatoses (atopic dermatitis, allergic dermatitis, chemical dermatitis, and psoriasis), sun damage (ultraviolet (UV) damage), and infections. Inhibition of CRM1, studied most comprehensively with LMB, showed minimal effects on normal keratinocytes and exerted anti-inflammatory activity on keratinocytes subjected to UV, TNFa, or other inflammatory stimuli. Inhibition of CRM1 can also upregulate the activity of NRF2 (nuclear factor erythroid 2-related factor 2), and NRF2 can protect keratinocytes from oxidative damage. LMB induces apoptosis of keratinocytes infected with oncogenic human papillomavirus (PV) strains such as IPV16, but does not induce apoptosis of uninfected keratinocytes.

CRM1 also mediates the transport of key neuroprotective proteins that may be useful for neurodegenerative diseases including Parkinson's disease (PD), Alzheimer's disease, and amyotrophic lateral sclerosis. For example, by (1) forcing nuclear retention of key neuroprotective regulatory factors such as NRF2, parking in neuronal cells, and/or (2) effecting the inhibition of the transcriptional activity of NF-kB by sequestering 1XB to the nucleus of glial cells, the inhibition of CRM1 may slow or prevent neuronal cell death found in these disorders. There is also evidence showing that abnormal glial cell proliferation is associated with abnormalities in CRM1 levels or CRM1 functions.

Intact maturation of many viruses also requires intact nuclear export mediated primarily by CRM1. Viruses whose life cycle involves nuclear export and/or CRM1 itself include human immunodeficiency virus (HIV), adenovirus, simian retrovirus type I, Borna disease virus, influenza virus (conventional strains as well as HINL and avian HN1 strains), hepatitis B virus (BV) and hepatitis C virus (HCV), human papillomavirus (HPV), respiratory syncytial virus (RSV), Dungee, severe acute respiratory syndrome coronavirus, yellow fever virus, west nile virus, herpes simplex virus (SV), cytomegalovirus (CMV), and Merkel cell polyomavirus (MCV).

The HIV-1Rev protein, which passes through the nucleolus and shuttles between the nucleus and cytoplasm, facilitates export of unspliced and singly spliced HIV transcripts containing Rev response element (RRE) RNA via the CRM1 export pathway. Inhibition of Rev-mediated RNA transport achieved using CRM1 inhibitors such as LepB or PKF050-638 can prevent the transcriptional process of HIV-1, inhibit the production of new HIV-1 virions, and thereby reduce HIV-1 levels.

Dengue virus (DENV) is the causative agent of the common arthropod-borne viral disease, Dengue fever (DF), and its more severe and potentially fatal form, Dengue hemorrhagic fever (DHF). DHF appears to result from an over-exuberant inflammatory response to DENV NS5 is the largest and most conserved protein of DENV CRM1 regulates the transport of NS5 from the nucleus to the cytoplasm, where most of the functions of NS5 are mediated. Inhibition of CRM1-mediated export of NS5 can result in altered virus-producing kinetics and reduced induction of the inflammatory chemokine interleukin-8 (IL-8), providing a novel approach for the treatment of diseases caused by DENV and other medically important flaviviruses, including hepatitis C virus.

Other virus-encoded RNA-binding proteins that exit the nucleus using CRM1 include HSVI type tegument protein (P13/14 or HUA7), human CMV protein pp65, SARS coronavirus ORF3b protein, and RSV matrix (M) protein.

Interestingly, many of these diseases are associated with specific types of human cancers, including hepatocellular carcinoma (HCC) due to chronic HBV or HCV infection, cervical cancer due to HPV, and Merkel cell carcinoma associated with MCV. Therefore, CRM1 inhibitors have beneficial effects on both the viral infection process and the neoplastic transformation process caused by these viruses.

CRM1 controls the nuclear localization and thereby the activity of a variety of DNA metabolizing enzymes, including histone deacetylases (HDACs), histone acetyltransferases (HATs), and histone methyltransferases (HMTs).

CRM1 is also associated with other disorders. Leber's disorder, a hereditary disease characterized by degeneration of retinal ganglion cells and visual loss, is associated with the inaction of the CRM1 switch. There is also evidence showing that neurodegenerative disorders are associated with abnormal nuclear transport.

SUMMARY

The present invention aims to provide a triazole derivative, a method for preparing same, and use thereof, wherein the triazole derivative can be used as a CRM1 inhibitor for preparing a medicament for treating a disease related to CRM1 activity.

In order to achieve the above objective, the present invention adopts the following technical solutions:

Provided is a triazole derivative or a pharmaceutically acceptable salt thereof, wherein the triazole derivative has a structure as shown in formula I:

(I)

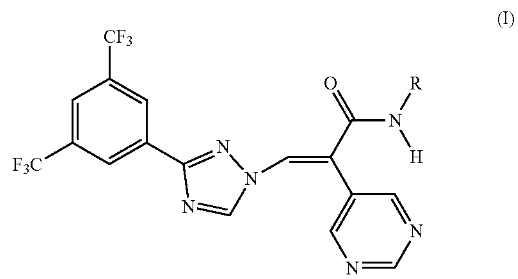

wherein,

R is selected from hydroxy, C1-6 alkyl, C1-6 alkoxy, and —C($OR^1$)(=$NR^2$);

$R^1$ and $R^2$ are independently hydrogen, C1-6 alkyl, C1-6 haloalkyl, or C1-6 alkoxy.

Further, R is selected from hydroxy, C1-4 alkyl, C1-4 alkoxy, and —C($OR^1$)(=$NR^2$);

$R^1$ and $R^2$ are independently hydrogen or C1-4 alkyl.

Further, the triazole derivative is selected from the following compounds:

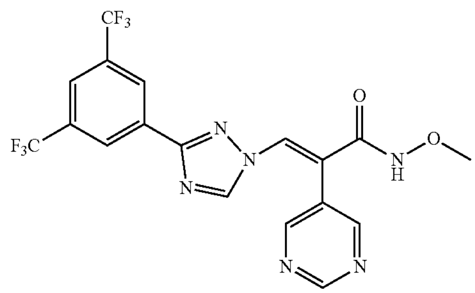 [SMILES: CONC(=O)/C(=C/n1cnc(-c2cc(C(F)(F)F)cc(C(F)(F)F)c2)n1)c1cncnc1]

,

-continued

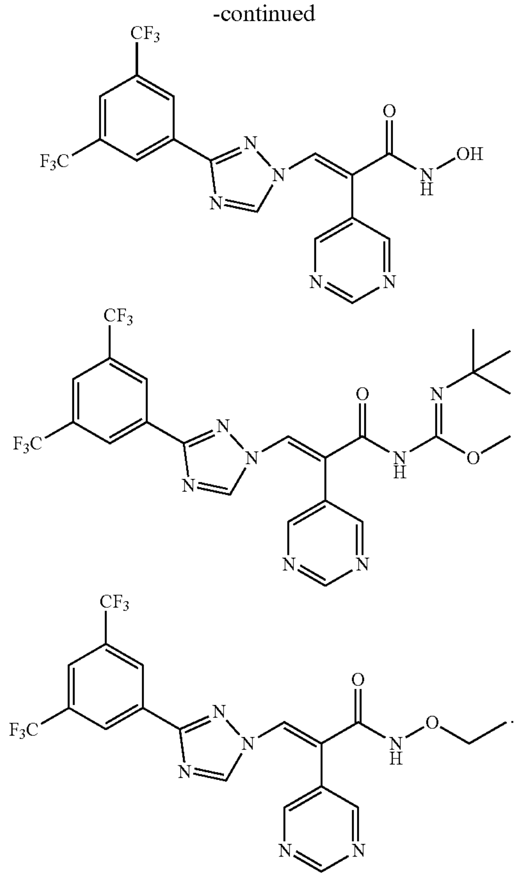

Provided is a method for preparing the triazole derivative or the pharmaceutically acceptable salt thereof described above, which is carried out according to the following route:

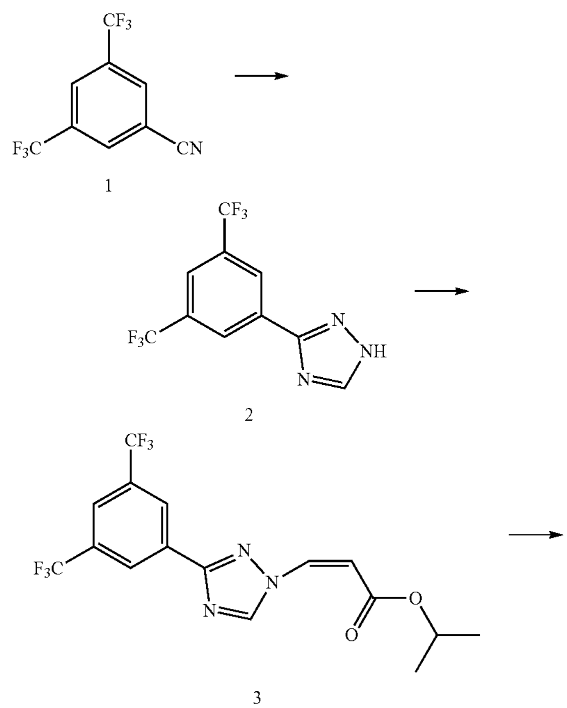

1

2

3

-continued

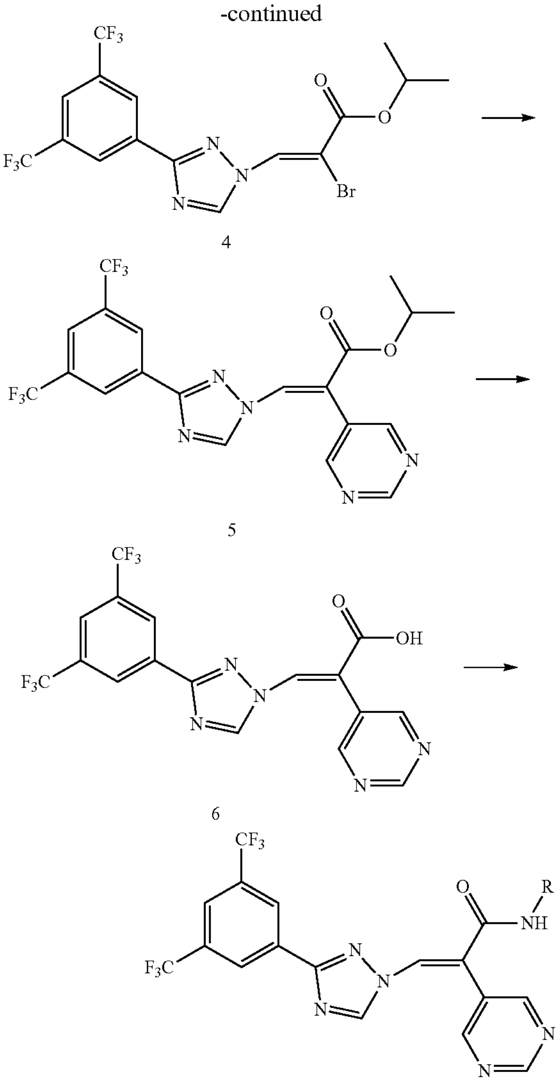

4

5

6

I

Provided is a pharmaceutical composition for treating a disease, disorder, or symptom related to CRM1 activity, comprising the triazole derivative or the pharmaceutically acceptable salt thereof described above, and a pharmaceutically acceptable carrier.

Provided is use of the triazole derivative or the pharmaceutically acceptable salt thereof described above in preparing a medicament for treating a disorder related to CRM1 activity.

Further, the disorder related to CRM1 activity is selected from a proliferative disorder, a cancer, an inflammatory disorder, an autoimmune disorder, a viral infection, an ophthalmic disorder, a neurodegenerative disorder, a disorder of abnormal tissue growth, a disorder related to food intake, an allergy, and a respiratory disorder.

Further, the disorder related to CRM1 activity is a cancer.

Further, the disorder related to CRM1 activity is multiple myeloma.

The beneficial effects are as follows: The cellular activity results indicate that compounds I and IV of the present invention are substantially equivalent to KPT-8602. The oral and intravenous half-lives of compound I are longer than those of KPT-8602, especially the oral half-life is about 2 times longer, and the intravenous and oral AUCs of compound I are much higher than those of KPT-8602, exhibiting better pharmacokinetic properties. Furthermore, compound I shows good safety.

BRIEF DESCRIPTION OF THE DRAWING

FIG. 1 shows the results of in vivo toxicity assay of compound I in BALB/C.

DETAILED DESCRIPTION

Definition of the Compounds

The compounds of the present invention include those generally described above, and are further described by the classes, subclasses, and species disclosed herein. As used herein, the following definitions shall be used unless otherwise specified. For the purposes of the present invention, these chemical elements are identified in accordance with the Periodic Table of the Elements (CAS version) and *Handbook of Chemistry and Physics* (75th Edition).

Unless otherwise stated within this specification, the nomenclature used in this specification generally follows the examples and rules stated in the *Nomenclature of Organic Chemistry*, Sections A, B, C, D, E, F, and H, which is incorporated by reference herein for its exemplary chemical structure names and rules on naming chemical structures.

The compounds of the present invention may have asymmetric centers, chiral axes, and chiral planes, and exist as racemates, racemic mixtures, and individual diastereomers or enantiomers, with all possible isomers and mixtures thereof (including optical isomers) being included in the present invention.

The "halogen" as used herein includes fluorine, chlorine, bromine, and iodine atoms. It is particularly preferably a fluorine or chlorine atom.

The "alkyl" as used herein includes linear or branched hydrocarbon groups having 1-15 carbon atoms, preferably 1-10 carbon atoms, more preferably 1-6 carbon atoms, and further preferably 1-4 carbon atoms. Examples of the alkyl include: methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl, and the like.

The "alkoxy" as used herein means a group in which the above-mentioned "alkyl" is bonded to an oxygen atom. Examples of the alkoxy include: methoxy, ethoxy, n-propoxy, isopropoxy, n-butoxy, tert-butoxy, isobutoxy, sec-butoxy, pentyloxy, isopentyloxy, hexyloxy, and the like.

Preferred embodiments of the "alkoxy" include: methoxy, ethoxy, n-propoxy, isopropoxy, and tert-butoxy.

The "haloalkyl" as used herein includes a group in which hydrogen atom(s) bonded to carbon atom(s) of the "alkyl" described above are replaced with one or more "halogen" described above. Examples of the haloalkyl include: monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-difluoropropan-2-yl, and the like.

Embodiments of the "haloalkyl" include trifluoromethyl and trichloromethyl.

The present invention provides a composition, comprising the compound of the present invention or a pharmaceutically acceptable derivative thereof, and a pharmaceutically acceptable carrier, adjuvant, or vehicle. The amount of the compound in the composition of the present invention is such that it is effective in moderately inhibiting CRM1 in a biological sample or a patient. In certain embodiments, a composition of the present invention is formulated for administration to a patient in need of such a composition. As used herein, the term "patient" means an animal. In some embodiments, the animal is a mammal. In certain embodiments, the patient is a veterinary patient (i.e., a non-human mammal patient).

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants, or vehicles that may be used in the composition of the present invention include, but are not limited to, ion exchangers, alumina, aluminum stearate, lecithin, serum proteins (such as human serum albumin), buffer substances (such as phosphates), glycine, sorbic acid, potassium sorbate, partial glyceride mixtures of saturated vegetable fatty acids, water, salts or electrolytes (such as protamine sulfate, disodium hydrogen phosphate, potassium hydrogen phosphate, sodium chloride, zinc salts), colloidal silica, magnesium trisilicate, polyvinylpyrrolidone, cellulose-based substances, polyethylene glycol, sodium carboxymethylcellulose, polyacrylates, waxes, polyethylene-poly oxypropylene block polymers, ethylene glycol, and lanolin.

The method for preparing the triazole derivative or the pharmaceutically acceptable salt thereof is carried out according to the following route:

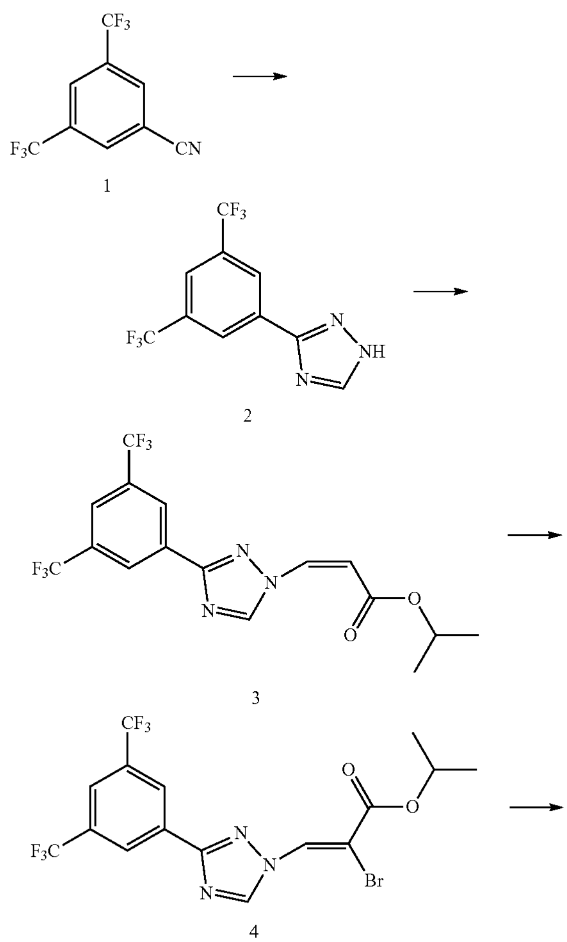

1

2

3

4

-continued

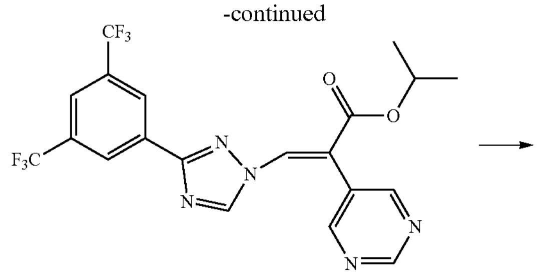

5

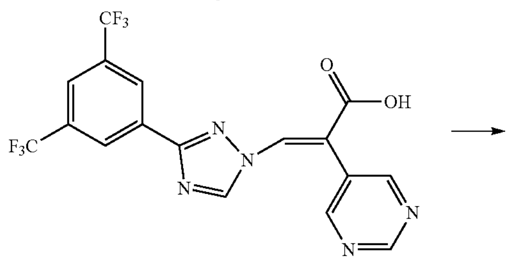

6

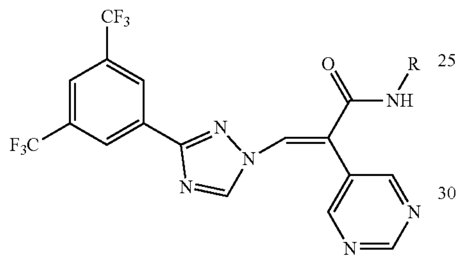

I wherein, in the reaction formula, each group R is defined as described previously; formula (1) is reacted under the action of sodium hydrosulfide to give formula (2); formula (2) is subjected to nucleophilic substitution to give formula (3); formula (3) is then reacted under the action of bromine water and triethylamine to give (4); formula (4) is subjected to a coupling reaction to give (5); formula (5) is hydrolyzed into a carboxylic acid of formula (6) under the action of LiOH; and formula (6) is condensed with an amine substrate to give a compound of formula I.

The method for preparing the compound of the present invention is detailed below:

A cyano group of compound 1 is reacted under the action of sodium hydrosulfide and magnesium chloride to give thioformamide, and then, under the conditions of hydrazine hydrate and formic acid, triazole 2 is generated. Triazole 2 is then coupled with (Z)-isopropyl 3-iodoacrylate under the catalytic action of triethylenediamine to give compound 3. Then, a double bond portion of compound 3 is subjected to an addition reaction with liquid bromine, and one molecule of bromine is removed under the action of triethylamine to give key intermediate 4. Next, intermediate 4 is separately subjected to Suzuki coupling, under the catalytic action of bis(triphenylphosphine)palladium dichloride, with a plurality of nitrogen-containing aromatic groups with boric acid structure to give compounds 5 connected with different nitrogen-containing aromatic groups. Finally, an ester bond of compound 5 is hydrolyzed into carboxylic acid compound 6 under the action of LiOH, and carboxylic acid compound 6 is further condensed to give a target compound of formula I.

The present invention is further illustrated in detail below with reference to the accompanying drawing and specific examples, but the present invention should not be construed as being limited thereto. Modifications or substitutions to the methods, procedures, or conditions of the present invention without departing from the spirit and scope of the present invention shall all fall in the scope of the present invention. In the examples, experimental procedures without specified conditions and reagents without stated formulations are all in accordance with the conventional conditions in the art.

EXAMPLE 1

I. Synthesis of Compounds

The preparation of the compounds of the present invention could be carried out as follows:

Route Design and Synthesis of Compound I

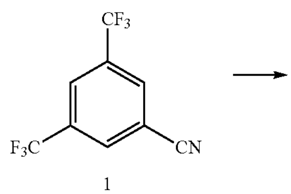

1

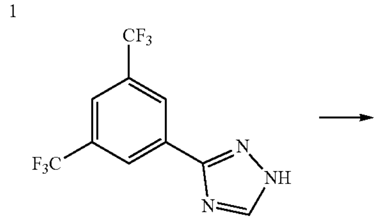

2

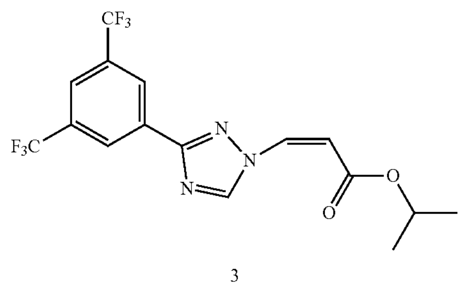

3

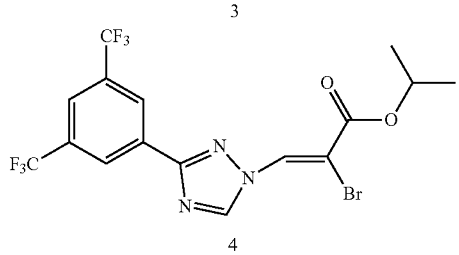

4

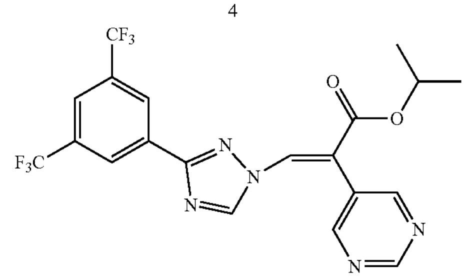

5

-continued

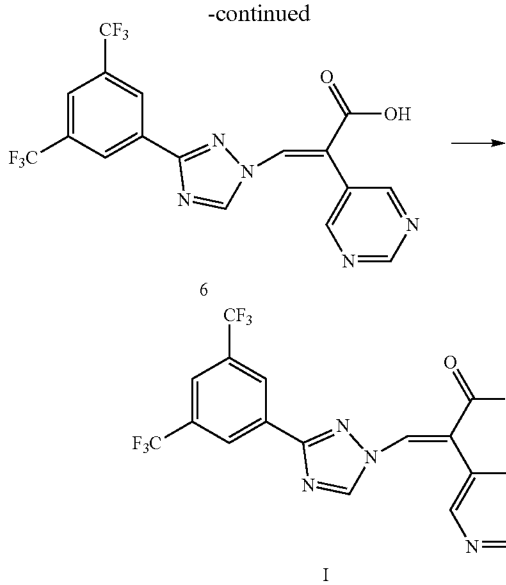

6

I

Synthesis of (Z)-isopropyl 3-(3-(3,5-bis(trifluoromethyl)phenyl)-1H-1,2,4-triazol-1-yl)acrylate (3)

In a 250 mL eggplant-shaped flask, 3,5-bis(trifluoromethyl)benzonitrile 1 (10 g, 41.8 mmol) was added and dissolved in a DMF solution (50 mL). NaSH (7.8 g, 83.7 mmol) and $MgCl_2$ (8.5 g, 41.8 mmol) were added sequentially, and the reaction mixture was stirred at room temperature for 3 h. After the reaction was completed as monitored by TLC, the reaction solution was poured into an ice-water mixed solution (500 mL). The mixture was extracted with ethyl acetate (100 mL×3). The organic phases were combined, washed with a saturated sodium chloride solution (100 mL×1), dried over anhydrous $Na_2SO_4$, filtered, and distilled under reduced pressure to remove the solvent, thus giving crude 3,5-bis(trifluoromethyl)benzothioamide (10.9 g, 95.1% yield, 84% purity) as a yellow oily liquid (MS (ESI) m/z 274.35 [M+H]+), which was used directly in the next step.

In a 250 mL eggplant-shaped flask, 3,5-bis(trifluoromethyl)benzothioamide (10.9 g, 39.8 mmol) was added and dissolved in a DMF solution (30 mL), and 80% hydrazine hydrate (5.1 mL, 83.6 mmol) was added dropwise thereto at room temperature. The mixture was stirred for 1 h, and then formic acid (30 mL) was added dropwise thereto. The reaction mixture was then stirred at 90° C. for another 3 h. After the reaction was completed as monitored by TLC, the reaction solution was cooled to room temperature and then poured into purified water (600 mL). The mixture was extracted with ethyl acetate (100 mL×3). The organic phases were combined, washed with a saturated sodium bicarbonate solution (300 mL×3) and a saturated sodium chloride solution (100 mL×1), dried over anhydrous $Na_2SO_4$, filtered, and distilled under reduced pressure to remove the solvent, thus giving a crude compound. The crude compound was stirred with n-hexane (200 mL×3) for washing, filtered, and dried to give 3-(3,5-bis(trifluoromethyl)phenyl)-1H-1,2,4-triazole 2 (8.5 g, 76.0% yield, 90% purity) as a white solid. $^1$H NMR (400 MHz, $CDCl_3$)) δ 8.63 (s, 2H, Ph), 8.40 (s, 1H, NCH), 8.02 (d, J=13.8 Hz, 1H, NCHCH), 7.95 (s, 1H, Ph), 6.74 (d, J=13.8 Hz, 1H, NCHCH) MS (ESI) m/z 279.89 $[M+H]^+$.

In a 250 mL eggplant-shaped flask, 3-(3,5-bis(trifluoromethyl)phenyl)-1H-1,2,4-triazole 2 (8.5 g, 30.2 mmol) was added and dissolved in DMF (40 mL), and DABCO (8.5 g, 75.5 mmol) was added thereto. The mixture was stirred at room temperature for 30 min, and then (Z)-ethyl 3-iodoacrylate (7.5 g, 33.2 mmol) was added dropwise to the reaction solution. The reaction mixture was then stirred at room temperature for another 3 h. After the reaction was completed as monitored by TLC, the reaction solution was poured into an ice-water mixed solution (400 mL). The mixture was extracted with ethyl acetate (80 mL×3). The organic phases were combined, washed with a saturated sodium chloride solution (100 mL×1), dried over anhydrous $Na_2SO_4$, filtered, and distilled under reduced pressure to remove the solvent, thus giving a crude compound. The resulting crude product was purified by column chromatography (PE/EtOAc=25:1) to give compound (Z)-ethyl 3-(3-(3,5-bis(trifluoromethyl)phenyl)-1H-1,2,4-triazol-1-yl) acrylate 3 (7.9 g, 68.2% yield, 98% purity) as a white solid. $^1$H NMR (400 MHz, $CDCl_3$)) δ 8.63 (s, 2H, Ph), 8.40 (s, 1H, NCH), 8.02 (d, J=13.8 Hz, 1H, NCHCH), 7.95 (s, 1H, Ph), 6.74 (d, J=13.8 Hz, 1H, NCHCH), 4.87 (m, 1H, CH), 1.36 (t, J=7.1 Hz, 6H, Me). MS (ESI) m/z 394.23 $[M+H]^+$.

Synthesis of (Z)-isopropyl 3-(3-(3,5-bis(trifluoromethyl)phenyl-triazol-1-yl)-2-bromoacrylate (4)

In a 250 mL eggplant-shaped flask, (Z)-ethyl 3-(3-(3,5-bis(trifluoromethyl)phenyl)-1H-1,2,4-triazol-1-yl)acrylate 3 (7.9 g, 20.6 mmol) obtained previously was dissolved in dichloromethane (40 mL), and liquid bromine (6.6 g, 41.2 mmol) was slowly added dropwise thereto over 30 min. The reaction mixture was then stirred at room temperature for 8 h. After the reaction was completed as monitored by TLC, the reaction solution was poured into an ice-water mixed solution (100 mL). The mixture was extracted with dichloromethane (50 mL×3). The organic phases were combined, washed with a saturated sodium bisulfite solution (100 mL×3) and a saturated sodium chloride solution (50 mL×1), dried over anhydrous $Na_2SO_4$, filtered, and distilled under reduced pressure to remove the solvent. Separation and purification by column chromatography (PE/EtOAc=50:1) were performed to give isopropyl 3-(3-(3,5-bis(trifluoromethyl)phenyl)-1H-1,2,4-triazol-1-yl)-2,3-dibromopropionate (10.3 g, 92.7% yield, 95% purity) as a white solid. MS (ESI) m/z 551.97 $[M+H]^+$.

The intermediate isopropyl 3-(3-(3,5-bis(trifluoromethyl) phenyl)-1H-1,2,4-triazol-1-yl)-2,3-dibromopropionate (103 g, 19.1 mmol) obtained in the previous step was weighed into a 250 mL eggplant-shaped flask and dissolved in tetrahydrofuran (40 mL). The reaction solution was stirred for 10 min under an ice bath, and then triethylamine (3.9 g, 38.2 mmol) was added dropwise thereto. The reaction mixture was stirred for another 30 min, and then placed at room temperature and stirred for another 6 h. After the reaction was completed as monitored by TLC, an ice-water mixed solution (100 mL) was added to the reaction solution. The mixture was extracted with ethyl acetate (50 mL×3). The organic phases were combined, washed with a saturated sodium chloride solution (50 mL×1), dried over anhydrous $Na_2SO_4$, filtered, and distilled under reduced pressure to remove the solvent. Separation and purification by column chromatography (PE/EtOAc=50:1) were performed to give (Z)-ethyl 3-(3-(3,5-bis(trifluoromethyl)phenyl)-1H-1,2,4-triazol-1-yl)-2-bromoacrylate 4 (7.7 g, 88.2% yield, 96% purity) as a white solid. $^1$H NMR (400 MHz, CDCl3) δ 8.75

(s, 1H, NCH), 8.56 (s, 2H, Ph), 7.93 (s, 1H, Ph), 7.65 (s, 1H, CBrCH), 4.38 (m, 1H, CH), 1.37 (t, J=7.1 Hz, 6H, Me). MS (ESI) m/z 473.09 $[M+H]^+$.

Synthesis of (E)-isopropyl 3-(3-(3,5-bis(trifluoromethyl)phenyl)-1H-1,2,4-triazol-1-yl)-2-(pyrimidin-5-yl) acrylate (5)

The important intermediate 4 (200 mg, 0.44 mmol) and 5-pyrimidineboronic acid (81.9 mg, 0.66 mmol) were weighed into a 25 mL three-necked flask and dissolved in a mixed solution of dioxane (5 mL) and water (1 mL). Sodium acetate (86.4 mg, 0.88 mmol) was then weighed into the reaction solution. The mixture was purged with nitrogen 3 times and stirred at room temperature. $Pd(PPh_3)Cl_2$ (30.9 mg, 0.04 mmol) was then added to the reaction solution, and the mixture was again purged with nitrogen 3 times and stirred overnight at 80° C. After the reaction was completed as monitored by TLC, the reaction solution was cooled to room temperature, and purified water (50 mL) was added thereto. The mixture was extracted with ethyl acetate (15 mL×3). The organic phases were combined, washed with a saturated sodium chloride solution (20 mL×1), dried over anhydrous $Na_2SO_4$, filtered, and distilled in vacuum to remove the solvent, thus giving a crude compound. The crude compound was separated and purified by column chromatography (PE/EtOAc=8:1) to give (E)-ethyl 3-(3-(3,5-bis(trifluoromethyl)phenyl)-1H-1,2,4-triazol-1-yl)-2-(pyrimidin-5-yl)acrylate 5 (125.3 mg, 62.3% yield, 93% purity) as a white solid. PNMR (400 MHz, $CDCl_3$)) δ 9.28 (s, 1H, Pyrimidine), 8.89 (s, 2H, Pyrimidine), 8.72 (s, 1H, NCH), 8.59 (s, 2H, Ph), 7.96 (s, 1H, Ph), 7.40 (s, 1H, COCCH), 4.85 (m, 1H, CH), 1.36 (t, J=7.2 Hz, 6H, Me). MS (ESI) m/z 472.17 $[M+H]^+$.

Synthesis of (E)-3-(3-(3,5-bis(trifluoromethyl)phenyl)-1H-1,2,4-triazol-1-yl)-2-(pyrimidin-5-yl)propenecarboxylic acid (6)

In a 25 mL eggplant-shaped flask, 5 (125.3 mg, 0.27 mmol) was dissolved in tetrahydrofuran (3 mL). The reaction solution was stirred for 10 min under an ice bath, and then a solution of LiOH $H_2O$ (45.3 mg, 1.08 mmol) in water (1 mL) was added dropwise thereto. After stirring for another 30 min, the reaction mixture was placed at room temperature and stirred overnight. After the reaction was completed as monitored by TLC, an ice-water mixed solution (10 mL) was poured into the reaction solution. The solution was adjusted to pH 2-3 with 4 N hydrochloric acid, and extracted with ethyl acetate (5 mL×3). The organic phases were combined, washed with a saturated sodium chloride solution (20 mL×1), dried over anhydrous $Na_2SO_4$, filtered, and distilled under reduced pressure to remove the solvent, thus giving relatively pure compound (E)-3-(3-(3,5-bis(trifluoromethyl)phenyl)-1H-1,2,4-triazol-1-yl)-2-(pyrimidin-5-yl) acrylic acid (99.4 mg, 85.8% yield, 89% purity) as a white solid, which was used directly in the next step. MS (ESI) m/z 427.92 $[M-H]^-$.

Synthesis of (E)-3-(3-(3,5-bis(trifluoromethyl)phenyl)-1H-1,2,4-triazol-1-yl)-N-methoxy-2-(pyrimidin-5-yl)acrylamide (I)

In a 25 mL eggplant-shaped flask, 6 (125.3 mg, 0.27 mmol) was dissolved in dichloroethane (3 mL). The reaction solution was stirred for 10 min under an ice bath, and then EDCI (20.3 mg, 1.08 mmol) and HOBT (70.5 mg, 1.5 mmol) were added thereto. After stirring for another 30 min, the reaction mixture was placed at room temperature. DIPEA (54.5 mg, 3.0 mmol) and methoxyhydroxylamine hydrochloride (23.4 mg, 1.0 mmol) were added dropwise, and the mixture was stirred overnight. After the reaction was completed as monitored by TLC, an ice-water mixed solution (10 mL) was poured into the reaction solution. The mixture was extracted with ethyl acetate (5 mL×3). The organic phases were combined, washed with a saturated sodium chloride solution (20 mL×1), dried over anhydrous $Na_2SO_4$, filtered, and distilled under reduced pressure to remove the solvent, thus giving compound (E)-3-(3-(3,5-bis(trifluoromethyl)phenyl)-1H-1,2,4-triazol-1-yl)-N-methoxy-2-(pyrimidin-5-yl)acrylamide (35.4 mg, 40% yield, 89% purity) as a white solid. $^1H$ NMR (400 MHz, CDCl3) δ 8.78 (d, J=5.9 Hz, 2H, Pyridine), 8.40 (s, 2H, Ph), 8.33 (s, 1H, NCH), 7.92 (s, 1H, Ph), 7.87 (s, 1H, COCCH), 7.28 (d, J=1.6 Hz, 2H, Pyridine), 4.34 (t, J=7.1 Hz, 3H, Me). MS (ESI) m/z 459.10 $[M+H]^+$.

The specific compounds synthesized and their names are given in the table below.

| Compound | Structure | Chemical name and analytical data |
|---|---|---|
| I | 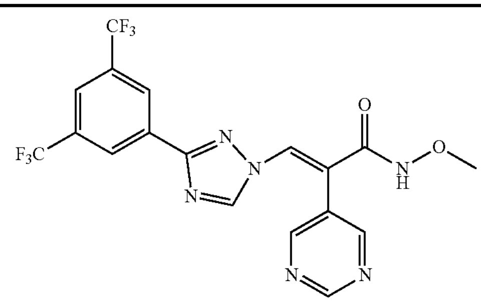 | (E)-3-(3-(3,5-Bis(trifluoromethyl)phenyl)-1H-1,2,4-triazol-1-yl)-N-methoxy-2-(pyrimidin-5-yl)acrylamide $^1H$ NMR (400 MHz, $CDCl_3$) δ 8.78 (d, J = 5.9 Hz, 2H, Pyridine), 8.40 (s, 2H, Ph), 8.33 (s, 1H, NCH), 7.92 (s, 1H, Ph), 7.87 (s, 1H, COCCH), 7.28 (d, J = 1.6 Hz, 2H, Pyridine), 4.34 (t, J = 7.1 Hz, 3H, Me), $^{13}C$ NMR ($CDCl_3$) δ 159.8, 158.1, 154.4, 147.7, 131.8, 131.2, 129.4, 128.6, 124.7, 123.1, 111.6, 130.4, 121.0, 64.4; Mass Spectrometry: HRMS-EI (m/z): Calcd for $C_{18}H_{12}F_6N_6O_2$ $[M + H]^+$. 459.0998. Found 459.0999. |

-continued

| Compound | Structure | Chemical name and analytical data |
|---|---|---|
| II | 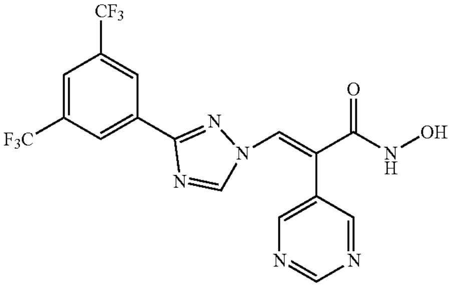 [SMILES: O=C(NO)/C(=C/n1cnc(-c2cc(C(F)(F)F)cc(C(F)(F)F)c2)n1)c1cncnc1] | (E)-3-(3-(3,5-Bis(trifluoromethyl)phenyl)-1H-1,2,4-triazol-1-yl)-N-hydroxy-2-(pyrimidin-5-yl)acrylamide $^{1}$H NMR (400 MHz, $CDCl_3$) δ 8.78 (d, J = 5.9 Hz, 2H, Pyridine), 8.40 (s, 2H, Ph), 8.33 (s, 1H, NCH), 7.92 (s, 1H, Ph), 7.87 (s, 1H, COCCH), 7.28 (d, J = 1.6 Hz, 2H, Pyridine); $^{13}$C NMR ($CDCl_3$) δ 161.6, 159.8, 158.1, 154.4, 147.7, 131.8, 131.2, 130.4, 129.4, 128.6, 124.7, 123.1, 121.0; Mass Spectrometry: HRMS-EI (m/z): Calcd for $C_{17}H_{10}F_6N_6O_2$ $[M + H]^+$, 445.0842. Found 445.0849. |
| III | 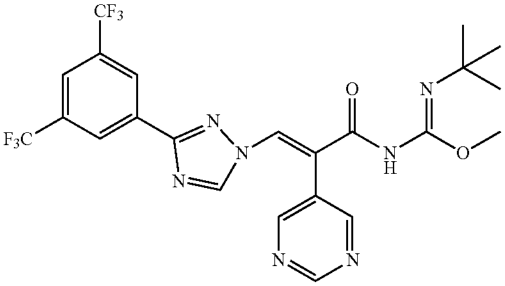 | Methyl(Z)-N-((E)-3-(3-(3,5-bis(trifluoromethyl)phenyl)-1H-1,2,4-triazol-1-yl)-2-(pyrimidin-5-yl)acryloyl)-N'-(tert-butyl)carbamate $^{1}$H NMR (400 MHz, CDCl3) δ 8.78 (d, J = 5.9 Hz, 2H, Pyridine), 8.40 (s, 2H, Ph), 8.33 (s, 1H, NCH), 7.92 (s, 1H, Ph), 7.87 (s, 1H, COCCH), 7.28 (d, J = 1.6 Hz, 2H, Pyridine), 1.17 (s, 9H, Me); 13C NMR (CDCl3) δ 161.6, 159.8, 158.1, 154.4, 147.7, 131.8, 131.2, 130.4, 129.4, 128.6, 124.7, 123.1, 121.0, 84.2, 28.4; Mass Spectrometry: HRMS-EI (m/z): Calcd for C22H18F6N6O2 [M + H]+, 545.1366. Found 545.1370. |
| IV | 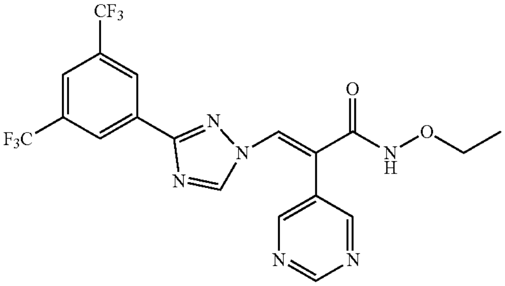 [SMILES: CCONC(=O)/C(=C/n1cnc(-c2cc(C(F)(F)F)cc(C(F)(F)F)c2)n1)c1cncnc1] | (E)-3-(3-(3,5-Bis(trifluoromethyl)phenyl)-1H-1,2,4-triazol-1-yl)-N-ethoxy-2-(pyrimidin-5-yl)acrylamide $^{1}$H NMR (400 MHz, $CDCl_3$) δ 8.78 (d, J = 5.9 Hz, 2H, Pyridine), 8.40 (s, 2H, Ph), 8.33 (s, 1H, NCH), 7.92 (s, 1H, Ph), 7.87 (s, 1H, COCCH), 7.28 (d, J = 1.6 Hz, 2H, Pyridine), 3.57 (m, 2H, $CH_2$) 1.34 (m, 3H, Me). $^{13}$C NMR ($CDCl_3$) δ 159.8, 158.1, 154.4, 147.7, 131.8, 131.2, 129.4, 128.6, 124.7, 123.1, 111.6, 130.4, 121.0, 65.4, 12.3; Mass Spectrometry: HRMS-EI (m/z): Calcd for $C_{19}H_{14}F_6N_6O_2$ $[M + H]^+$, 473.1155. Found 473.1159. |

II. Cell Line Inhibitory Activity

1. Cell Cryopreservation (1) Cells were harvested, centrifuged at 1000 rpm for 5 min at room temperature, and rinsed with PBS.

(2) The cells were then resuspended in a 1640 medium containing 7% DMSO and 10% fetal bovine serum.

(3) The cell suspension was aliquoted into cryopreservation tubes, placed in cell cryopreservation containers, cryopreserved at −80° C. overnight, and then stored in liquid nitrogen.

2. Cell Recovery and Culture (1) The cryopreservation tubes were removed from the liquid nitrogen tank, placed in warm water at 37° C., and gently shaken to thaw the cell liquid.

(2) The cells were transferred to a sterile centrifuge tube, and a 1640 medium containing 10% fetal bovine serum was added. The mixture was gently pipetted to give a suspension.

(3) The cells were centrifuged at 1000 rpm for 5 min at room temperature, and the supernatant was discarded. A 1640 medium containing 10% fetal bovine serum was added, and the mixture was gently pipetted to give a suspension.

(4) The suspension was transferred into a culture flask and cultured in an incubator (37° C., 5% $CO_2$, saturated humidity). After 1-2 days of culture, the medium was exchanged.

3. Cell Passage

The original medium was discarded. The cells were washed once with sterile PBS, incubated with 1 mL of 0.25% pancreatin for about 1 min, and then observed under a microscope. After most of the cells became round, the pancreatin was carefully aspirated, and a fresh medium was added to stop the digestion. The cells were pipetted to give a homogeneous cell suspension, and the cell suspension was transferred into a cell incubator for further culture.

4. Cytotoxicity Experiment (1) RPMI8226 cells in the logarithmic growth phase were added to a 384-well plate at 1000 cells/well in a volume of 18 μL/well and incubated at 37° C., 5% $CO_2$ for 24 h.

(2) The test compound at a stock concentration of 10 mM was diluted 10-fold with DMSO and then 100-fold with a serum-free 1640 medium to give a dilution at a working concentration of 10 μM containing 1% DMSO. 10 concentrations were then obtained by 2-fold serial dilution using a serum-free 1640 medium containing 1% DMSO, with the tenth concentration point being a solvent control group (no drug). The diluted compound was added into the plated cell plate at 2 μL/well to give final compound concentrations from 1000 nM (2-fold gradient dilution, 10 concentration gradients), and 4 replicates were set for each concentration. 1% DMSO was used as a solvent control and KPT-8602 as a positive control.

(3) The cells were incubated at 37° C. for 72 h, and 10 μL of Cell-Titer assay reagent was added to each well, followed by incubation in a cell incubator for 10 min.

(4) The mixture was well mixed by shaking and then assayed by the Cell-Titer program running on a microplate reader. The inhibition % and $IC_{50}$ values (μM) were calculated using GraphPad Prism 5.

The cellular activity results with the compounds are shown in the table below:

| Compound | RPMI8226 | Compound | RPMI8226 |
|---|---|---|---|
| KPT-8602 | 0.34 | I | 0.37 |
| II | 6.9 | III | 7.1 |
| IV | 0.54 | | |

The cellular activity results indicate that compounds I and IV were substantially equivalent to KPT-8602.

III. Pharmacokinetic Results of the Drugs in SD Rats

| | KPT-8602 | | I | |
|---|---|---|---|---|
| PK | iv (2 mg/kg) | po (10 mg/kg) | iv (2 mg/kg) | po (10 mg/kg) |
| $T_{1/2}$ (h) | 3.04 | 2.69 | 4.23 | 5.59 |
| $C_{max}$ (ng/mL) | — | 720 | — | 899 |
| $T_{max}$ (h) | — | 1 | — | 0.25 |
| Cl s, spp | 34.4 | 67.4 | 24.2 | 43.8 |
| $AUC_{0-t}$ | 963 | 2541 | 1301 | 3212 |
| $AUC_{0-inf}$ | 998 | 2595 | 1493 | 3893 |
| MRT | 2.48 | 3.85 | 2.49 | 7.65 |
| F (%) | — | 52.0 | — | 55.9 |

Conclusion: The oral and intravenous half-lives of compound I were longer than those of KPT-8602, especially the oral half-life was about 2 times longer, and the intravenous and oral AUCs of compound I were much higher than those of KPT-8602, exhibiting better pharmacokinetic properties.

IV. In Vivo Toxicity Assay of Candidate Compounds in BALB/C

25 BALB/C mice were randomly divided into the following 5 groups: solvent control group (Control), positive control KPT-8602 (30 mg/kg, once daily) group, KPT-8602 (60 mg/kg, once daily) group, compound I (30 mg/kg, once daily) group, and compound I (60 mg/kg, once daily) group, with 5 mice in each group. Each group was intragastrically given a test compound at a corresponding concentration at a dose of 3 mL/kg. KPT-8602 and compound I were administered daily for 21 consecutive days.

The compound solutions were prepared as follows:

Preparation of 10% Sulfobutyl-β-cyclodextrin:

5.0 g of sulfobutyl-β-cyclodextrin powder was weighed into a beaker, and 50 mL of citric acid buffer was pipetted into the beaker. After the powder was dissolved, the resulting solution was transferred into a container.

Preparation of Compound I:

24 mg of compound I was weighed, and 1.6 mL of a 20% aqueous polyethylene glycol solution was added. After complete dissolution, 6.4 mL of a 10% aqueous sulfobutyl-β-cyclodextrin solution was added, thus giving a test solution of compound I (3 mg/mL).

Preparation of KPT-8602:

24 mg of compound KPT-8602 was weighed, and 1.6 mL of a 20% aqueous polyethylene glycol solution was added. After complete dissolution, 6.4 mL of a 10% aqueous sulfobutyl-β-cyclodextrin solution was added, thus giving a test solution of KPT-8602 (3 mg/mL).

The results of body weight changes of the mice after the consecutive administration are shown in FIG. 1.

CONCLUSION

As shown in the FIGURE, two mice in the 60 mg/kg group of KPT-8602 died on day 7, and all died by day 10. The 30 mg/kg group of KPT-8602 showed a significant decrease in body weight. In contrast, the 30 mg/kg and 60 mg/kg groups of compound I still had body weights comparable to the blank after 21 days, showing good safety.

The invention claimed is:

1. A triazole derivative or a pharmaceutically acceptable salt thereof, wherein the triazole derivative has a structure as shown in formula I:

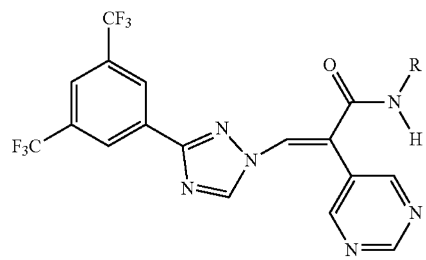

(I)

wherein,

R is selected from hydroxy, C1-6 alkoxy, and —C($OR^1$)(=$NR^2$); and $R^1$ and $R^2$ are independently hydrogen, C1-6 alkyl, C1-6 haloalkyl, or C1-6 alkoxy.

2. The triazole derivative or the pharmaceutically acceptable salt thereof according to claim 1, wherein R is selected from hydroxy, C1-4 alkoxy, and —C($OR^1$)(=$NR^2$); and $R^1$ and $R^2$ are independently hydrogen or C1-4 alkyl.

3. The triazole derivative or the pharmaceutically acceptable salt thereof according to claim 1, wherein the triazole derivative is selected from the following compounds:

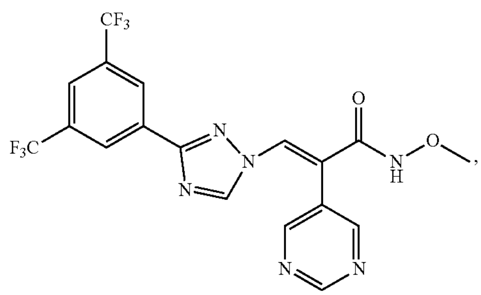

-continued

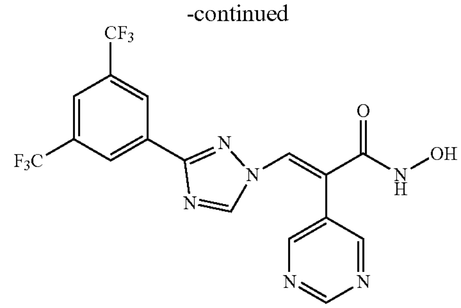

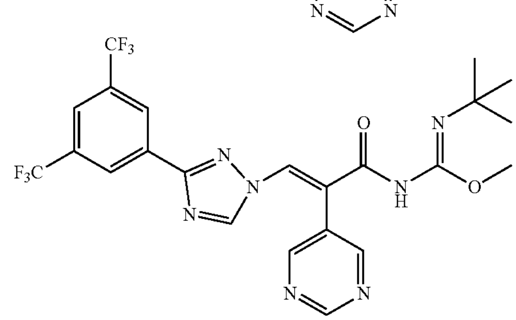

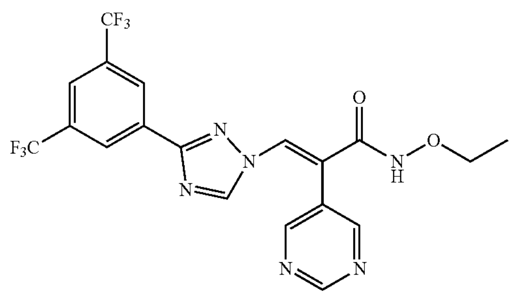

* * * * *